US011024796B2

(12) United States Patent
Kim et al.

(10) Patent No.: US 11,024,796 B2
(45) Date of Patent: Jun. 1, 2021

(54) METHOD OF MANUFACTURING AN ULTRASONIC PROBE

(71) Applicant: SAMSUNG MEDISON CO., LTD., Hongcheon-gun (KR)

(72) Inventors: Young-il Kim, Suwon-si (KR); Jong-keun Song, Yongin-si (KR); Tae-ho Jeon, Seoul (KR); Min-seog Choi, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 563 days.

(21) Appl. No.: 15/862,331

(22) Filed: Jan. 4, 2018

(65) Prior Publication Data

US 2018/0198056 A1 Jul. 12, 2018

(30) Foreign Application Priority Data

Jan. 11, 2017 (KR) .................. 10-2017-0004166

(51) Int. Cl.
*H04R 31/00* (2006.01)
*H01L 41/27* (2013.01)
(Continued)

(52) U.S. Cl.
CPC ............ *H01L 41/27* (2013.01); *A61B 8/4494* (2013.01); *B06B 1/06* (2013.01); *B06B 1/0607* (2013.01);
(Continued)

(58) Field of Classification Search
CPC ..... G10K 11/18; A61B 8/4494; B06B 1/0607; B06B 1/0622; H01L 41/27; G01N 29/2406
See application file for complete search history.

(56) References Cited

U.S. PATENT DOCUMENTS 6,669,644 B2 * 12/2003 Miller ................... B06B 1/0292
367/181
6,958,255 B2 * 10/2005 Khuri-Yakub ........ B06B 1/0688
438/118

(Continued)

FOREIGN PATENT DOCUMENTS

JP    2006-516368 A    6/2006
JP    2008-110060 A    5/2008

(Continued)

OTHER PUBLICATIONS

Communication dated Jun. 13, 2018, issued by the European Patent Office in counterpart European Patent Application No. 18151230.2.

(Continued)

*Primary Examiner* — Paul D Kim
(74) *Attorney, Agent, or Firm* — Sughrue Mion, PLLC

(57) ABSTRACT

Provided are an ultrasonic probe and a method of manufacturing the same. The method includes: forming a plurality of grooves by removing regions of a first insulating layer and a first silicon wafer from a first substrate including the first silicon wafer and the first insulating layer; bonding a second substrate including a second silicon wafer, a second insulating layer, and a silicon thin layer to the first substrate, such that the plurality of grooves turn into a plurality of cavities; removing the second silicon wafer from the second substrate; forming transducer cells on regions of the second insulating layer corresponding to the plurality of cavities; and forming a plurality of unit substrates by cutting the first substrate, the silicon thin layer, and the second insulating layer.

11 Claims, 9 Drawing Sheets

(51) Int. Cl.
*B06B 1/06* (2006.01)
*G01N 29/24* (2006.01)
*A61B 8/00* (2006.01)
*G10K 11/18* (2006.01)

(52) U.S. Cl.
CPC ....... *B06B 1/0622* (2013.01); *G01N 29/2406* (2013.01); *G10K 11/18* (2013.01)

(56) References Cited

U.S. PATENT DOCUMENTS

| | | |
|---|---|---|
| 7,285,897 B2 | 10/2007 | Fisher et al. |
| 7,441,321 B2 | 10/2008 | Baumgartner et al. |
| 7,451,651 B2 | 11/2008 | Woychik et al. |
| 7,732,992 B2 | 6/2010 | Wilser et al. |
| 8,740,800 B2 | 6/2014 | Wakabayashi et al. |
| 2006/0238067 A1 | 10/2006 | Dausch |
| 2007/0164632 A1* | 7/2007 | Adachi ................ B06B 1/0292 310/311 |
| 2007/0299345 A1* | 12/2007 | Adachi ................ B06B 1/0292 600/459 |
| 2008/0315331 A1* | 12/2008 | Wodnicki ............ G01S 7/52079 257/414 |
| 2011/0237952 A1 | 9/2011 | Ooishi et al. |
| 2012/0319535 A1 | 12/2012 | Dausch |
| 2013/0242705 A1* | 9/2013 | Kim ........................ H04R 31/00 367/181 |
| 2013/0338508 A1 | 12/2013 | Nakamura et al. |
| 2015/0326146 A1 | 11/2015 | Huang |

FOREIGN PATENT DOCUMENTS

| | | |
|---|---|---|
| JP | 2011-505206 A | 2/2011 |
| JP | 2013-5403 A | 1/2013 |
| WO | 2004/016036 A2 | 2/2004 |
| WO | 2004/016036 A3 | 2/2004 |
| WO | 2009/073753 A1 | 6/2009 |

OTHER PUBLICATIONS

Communication dated Jan. 16, 2018, issued by the Korean Intellectual Property Office in corresponding Korean Application No. 10-2017-0004166.

* cited by examiner

METHOD OF MANUFACTURING AN ULTRASONIC PROBE

CROSS-REFERENCE TO RELATED APPLICATION

This application claims the benefit of Korean Patent Application No. 10-2017-0004166, filed on Jan. 11, 2017, in the Korean Intellectual Property Office, the disclosure of which is incorporated herein in its entirety by reference.

BACKGROUND

1. Field

The present disclosure relates to ultrasonic probes and methods of manufacturing the same.

2. Description of the Related Art

Generally, an ultrasonic diagnostic apparatus transmits ultrasound waves to an object, such as a person or an animal, displays an image of a cross-section of tissue in the object by detecting echo signals reflected from the object, and provides information necessary for diagnosing a disease of the object. The ultrasonic diagnostic apparatus includes an ultrasonic probe for transmitting ultrasound waves to and receiving echo signals from the object.

An ultrasonic probe may include transducers that convert electrical signals into ultrasound signals or vice versa. Micromachined ultrasonic transducers (MUTs) that are an example of ultrasonic transducers may be classified into piezoelectric MUTs (pMUTs), capacitive MUTs (cMUTs), and magnetic MUTs (mMUTs) according to the conversion methods they use.

SUMMARY

Provided are ultrasonic probes and methods of manufacturing the same, capable of realizing various probe shapes.

Additional aspects will be set forth in part in the description which follows and, in part, will be apparent from the description, or may be learned by practice of the presented embodiments.

According to an aspect of an embodiment, a method of manufacturing an ultrasonic probe includes: forming a plurality of grooves by removing regions of a first insulating layer and a first silicon wafer from a first substrate including the first silicon wafer and the first insulating layer; bonding a second substrate including a second silicon wafer, a second insulating layer, and a silicon thin layer to the first substrate, such that the plurality of grooves turn into a plurality of cavities; removing the second silicon wafer from the second substrate; forming transducer cells on regions of the second insulating layer corresponding to the plurality of cavities; and forming a plurality of unit substrates by cutting the first substrate, the silicon thin layer, and the second insulating layer.

The method may further include reducing a thickness of the first silicon wafer by removing a part of the first silicon wafer.

The first silicon wafer may have a thickness of 30 to 150 µm after removing the part of the first silicon wafer.

The forming of the transducer cells may include: sequentially forming an electrically conductive material and a piezoelectric material on the second insulating layer; forming a first electrode and a piezoelectric layer by respectively patterning the electrically conductive material and the piezoelectric material; and forming a second electrode on the piezoelectric layer.

The piezoelectric layer may have a thickness of less than or equal to 10 µm.

Before forming the second electrode, the method may further include forming a third insulating layer covering the piezoelectric layer and the first electrode.

The plurality of unit substrates may be formed by deep reactive ion etching.

The forming of the plurality of unit substrates may include forming the plurality of unit substrates so that one or more transducer cells are provided for each of the plurality of unit substrates.

The forming of the plurality of unit substrates may include forming the plurality of unit substrates by removing regions of the first substrate, the silicon thin layer, and the second insulating layer that do not overlap the transducer cells.

The method may further include bonding the first substrate to a circuit substrate before forming the plurality of unit substrates.

The circuit substrate may be flexible.

The method may further include bonding the circuit substrate to a curved frame.

The frame may have a spherical shape.

According to an aspect of another embodiment, an ultrasonic probe includes: a plurality of unit substrates, each including a cavity formed therein and a silicon on insulator (SOI) structure; and a plurality of transducer cells arranged on the plurality of unit substrates and each including a piezoelectric layer.

The SOI structure may include a silicon wafer, a first insulating layer, and a silicon thin layer, and the silicon wafer of the SOI structure may have a thickness of 30 to 150 µm.

The cavity may be formed by a groove in the silicon wafer and an opening in the first insulating layer.

Each of the plurality of transducer cells may further include first and second electrodes separated from each other so that the piezoelectric layer is interposed therebetween.

The piezoelectric layer may have a thickness of less than or equal to 10 µm.

The ultrasonic probe may further include a circuit substrate provided on a bottom surface of the plurality of unit substrates.

The circuit substrate may be flexible.

The ultrasonic probe may further include a curved support member provided on a bottom surface of the circuit substrate.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
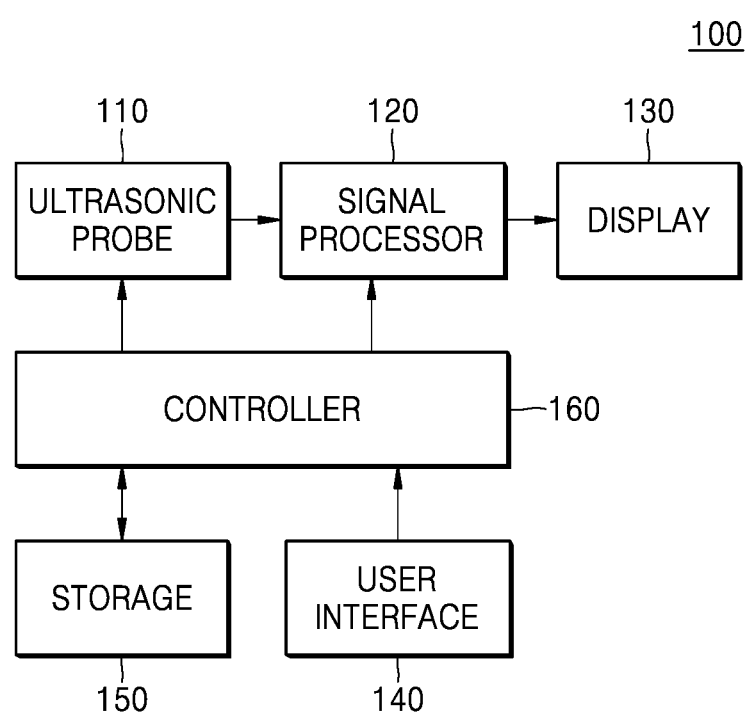
FIG. 1 is a block diagram of an ultrasonic diagnostic apparatus according to an embodiment.

Exemplary embodiments will be described more fully hereinafter with reference to the accompanying drawings, in which the same or corresponding elements are denoted by the same reference numerals. Descriptions of the same or corresponding elements will not be repeated below.

It will be understood that the terms "comprises," "comprising," "includes" and/or "including," if used herein, should not be construed as necessarily including various elements, components, steps, and/or operations stated in the specification, and do not preclude the exclusion of some of the stated elements, components, steps, and/or operations or addition of one or more other elements, components, steps and/or operations.

It will also be understood that when a layer or element is referred to as being "on" another layer or substrate, it can be directly on/beneath/on the left side of/on the right side of the other layer or substrate, or intervening layers may also be present therebetween. Accordingly, the embodiments are merely described below, by referring to the figures, to explain aspects.

It will be understood that, although the terms "first", "second", etc. may be used herein to describe various elements and/or components, these elements and/or components should not be limited by these terms. These terms are only used to distinguish one element or component from another element or component. Expressions such as "at least one of," when preceding a list of elements, modify the entire list of elements and do not modify the individual elements of the list.

In the present specification, an "object" may include a person or an animal, or a part of a person or an animal. For example, the object may include an organ such as the liver, the heart, the womb, the brain, a breast or the abdomen, or a blood vessel. Furthermore, a "user" refers to a medical professional, such as a doctor, a nurse, a medical laboratory technologist, an medical imaging expert, and an engineer who repairs a medical apparatus, but the user is not limited thereto.

FIG. 1 is a block diagram of an ultrasonic diagnostic apparatus 100 according to an embodiment. Referring to FIG. 1, the ultrasonic diagnostic apparatus 100 includes an ultrasonic probe 110 for transmitting or receiving ultrasound waves, a signal processor 120 for processing a signal applied by the ultrasonic probe 110 to thereby generate an image, a display 130 for displaying an image, a user interface 140 for receiving a user command, a storage 150 for storing various types of information, and a controller 160 for controlling all operations of the ultrasonic diagnostic apparatus 100.

The ultrasonic probe 110 transmits ultrasound waves to an object and receives echo signals corresponding to the ultrasound waves reflected from the object, as described in more detail below.

The signal processor 120 may process ultrasound data generated by the ultrasonic probe 110 to generate an ultrasound image. An ultrasound image may be at least one of a brightness (B) mode image representing a magnitude of an ultrasound echo signal reflected from an object as brightness, a Doppler (D) mode image showing an image of a moving object in the form of a spectrum by using a Doppler effect, a motion (M) mode image representing movement of an object at a specific position over time, an elastic mode image visualizing a difference between responses when compression is or is not applied to an object as an image, and a color (C) mode image representing a velocity of a moving object in colors by using a Doppler effect. Since an ultrasound image is generated by using currently available methods of generating an ultrasound image, a detailed description thereof will be omitted here. Accordingly, an ultrasound image according to an embodiment may include any of images taken in dimensional modes, such as a one-dimensional (1D) mode, a two-dimensional (2D) mode, a three-dimensional (3D) mode, and a four-dimensional (4D) mode.

The display 130 displays information processed by the ultrasonic diagnostic apparatus 100. For example, the display 130 may display an ultrasound image generated by the signal processor 120 as well as a graphical user interface (GUI) for requesting a user input.

The display 230 may include at least one of a liquid crystal display (LCD), a thin film transistor-LCD (TFT-LCD), an organic light-emitting diode (OLED), a flexible display, a 3D display, and an electrophoretic display. The ultrasonic diagnostic apparatus 100 may include two or more displays 130 according to its implementation configuration.

The user interface 140 refers to a means via which a user inputs data for controlling the ultrasonic diagnostic apparatus 100. The user interface 140 may include a keypad, a mouse, a touch panel, a track ball, etc. The user interface 140 is not limited thereto, and may further include various other input elements such as a jog wheel and a jog switch.

The touch panel may detect both a real touch where a pointer actually touches a screen and a proximity touch where the pointer approaches the screen while being separated from the screen by less than a predetermined distance. In the present specification, the term 'pointer' means a tool for touching a particular portion on or near the touch panel. Examples of the pointer may include a stylus pen and a body part such as a finger.

Furthermore, the touch panel may be formed as a touch screen that forms a layer structure with the display 130. The touch screen may be implemented as various types such as capacitive overlay, resistive overlay, infrared beam, surface acoustic wave, integral strain gauge, and piezoelectric touch screens. The touch screen is very useful because it functions as both the display 130 and the user interface 140.

Although not shown in FIG. 1, various sensors may be disposed within or near the touch panel so as to sense a touch. A tactile sensor is an example of the sensors designed for the touch panel to sense a touch. The tactile sensor is used to sense a touch of a particular object to a same or greater degree than the degree to which a human can sense the touch. The tactile sensor may detect various pieces of information including the toughness of a contact surface, the hardness of an object to be touched, and the temperature of a point to be touched.

A proximity sensor is another example of the sensors designed for the touch panel to sense a touch. The proximity sensor is a sensor that detects the presence of an object that is approaching or is located near a predetermined detection surface by using the force of an electromagnetic field or infrared light without any mechanical contact. Examples of the proximity sensor include a transmissive photoelectric sensor, a direct reflective photoelectric sensor, a mirror reflective photoelectric sensor, a high-frequency oscillation proximity sensor, a capacitive proximity sensor, a magnetic proximity sensor, and an infrared proximity sensor.

The storage 150 stores various types of information that are processed by the ultrasonic diagnostic apparatus 100.

For example, the storage 150 may store medical data related to diagnosis of the object, such as images, and algorithms or programs that are executed in the ultrasonic diagnostic apparatus 100.

The storage 150 may include at least one storage medium from among a flash memory-type storage medium, a hard disk-type storage medium, a multimedia card micro-type storage medium, card-type memories (e.g., an SD card, an XD memory, and the like), a Random Access Memory (RAM), a Static Random Access Memory (SRAM), a Read-Only Memory (ROM), an Electrically Erasable Programmable ROM (EEPROM), a PROM, a magnetic memory, a magnetic disc, and an optical disc. Furthermore, the ultrasonic diagnostic apparatus 100 may utilize web storage or a cloud server that functions as the storage 150 online.

The controller 160 controls all operations of the ultrasonic diagnostic apparatus 100. In other words, the controller 160 may control operations of the ultrasonic probe 110, the signal processor 120, the display 130, and other components described with reference to FIG. 1. For example, the controller 160 may control the signal processor 120 to generate an image by using a user command received via the user interface 140 or programs stored in the storage 150. The controller 160 may also control the display 130 to display the image generated by the signal processor 220.

Figure 2:
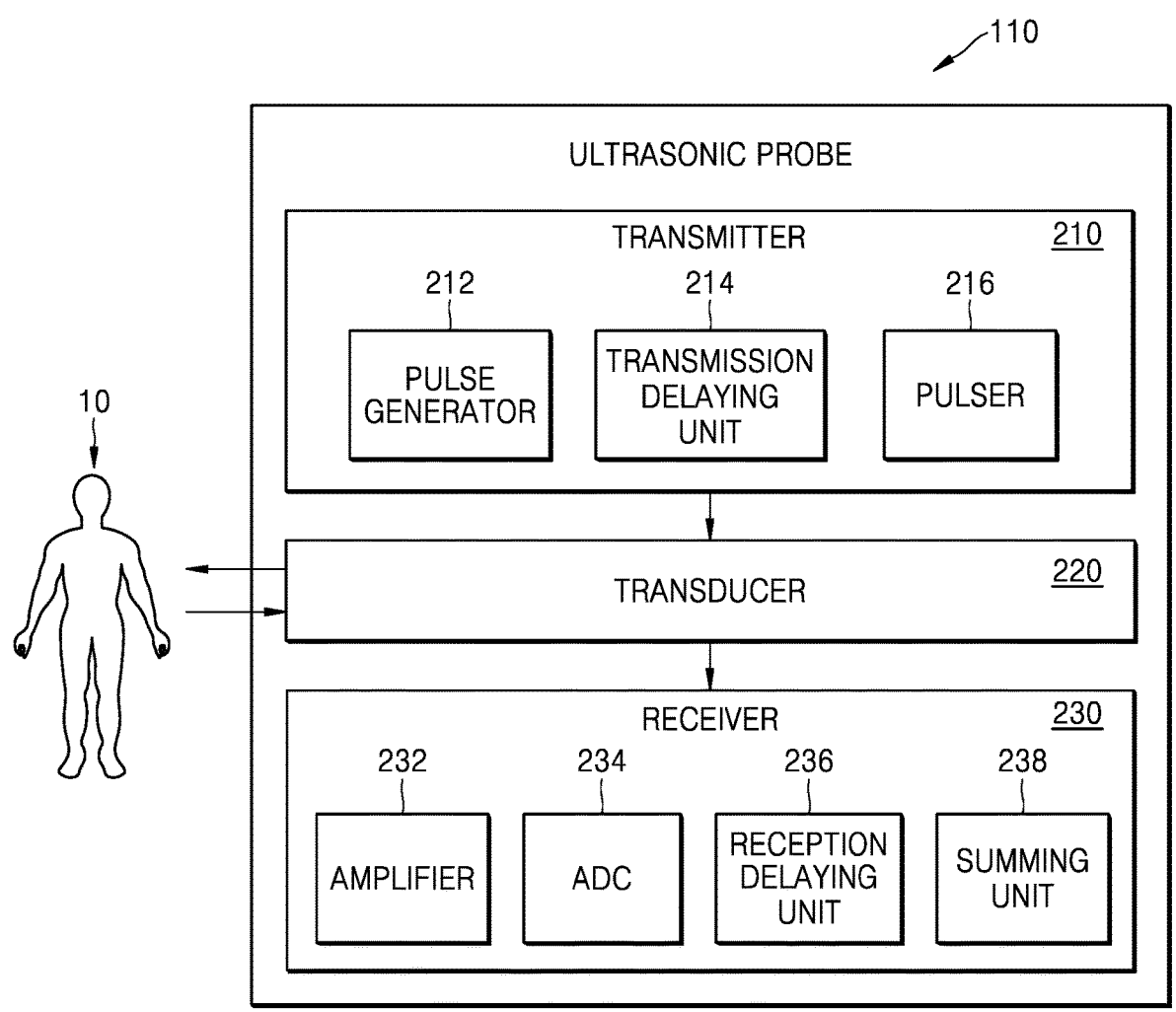
FIG. 2 is a block diagram of an ultrasonic probe included in the ultrasonic diagnostic apparatus of FIG. 1.

FIG. 2 is a block diagram of an ultrasonic probe included in the ultrasonic diagnostic apparatus of FIG. 1. Referring to FIG. 2, the ultrasonic probe 110 may transmit ultrasound waves to an object 10 and receive echo signals reflected from the object to thereby generate ultrasound data, and include a transmitter 210, a transducer 220, and a receiver 230.

The transmitter 210 supplies a driving signal to the transducer 220. The transmitter 210 includes a pulse generator 212, a transmission delaying unit 214, and a pulser 216.

The pulse generator 212 generates rate pulses for forming transmission ultrasound waves based on a predetermined pulse repetition frequency (PRF), and the transmission delaying unit 214 delays the rate pulses by delay times necessary for determining transmission directionality. The rate pulses which have been delayed respectively correspond to a plurality of transducer cells (400 of FIG. 3) included in the transducer 220. The pulser 216 applies a driving signal (or a driving pulse) to the transducer 210 based on timing corresponding to each of the rate pulses which have been delayed.

The transducer 220 transmits ultrasound waves to the object 10 in response to the driving signal applied by the transmitter 210 and receives echo signals corresponding to the ultrasound waves reflected by the object 10. The transducer 220 may include the plurality of transducer cells 400 that convert electrical signals into acoustic energy (or vice versa).

The receiver 230 generates ultrasound data by processing signals received from the transducer 220 and may include an amplifier 232, an analog-to-digital converter (ADC) 234, a reception delaying unit 236, and a summing unit 238.

The amplifier 232 amplifies received from the transducer 220, and the ADC 234 performs analog-to-digital conversion with respect to the amplified signals. The reception delaying unit 236 delays digital signals output by the ADC 234 by delay times necessary for determining reception directionality, and the summing unit 238 generates ultrasound data by summing signals processed by the reception delaying unit 236. A reflection component from a direction determined by the reception directionality may be emphasized by a summing process performed by the summing unit 238.

The transmitter 210 and the receiver 230 of the ultrasonic probe 110 may be formed as at least one chip on a single substrate. Here, the single substrate may be formed of silicon (Si), ceramic, or a polymer-based material. Each block or at least two blocks in the transmitter 210 and the receiver 230 may be formed as a single chip, or blocks in the transmitter 210 and the receiver 230 corresponding to each transducer cell may be formed as a single chip. Thus, a substrate including at least one of the transmitter 210 and the receiver 230 is referred to as a circuit substrate. The circuit substrate may mean a substrate including all or some of the chips included in the ultrasonic probe 110.

In addition, the ultrasound probe 110 may further include some components included in the signal processor 120, the display 130, and the input interface 140.

Figure 3:
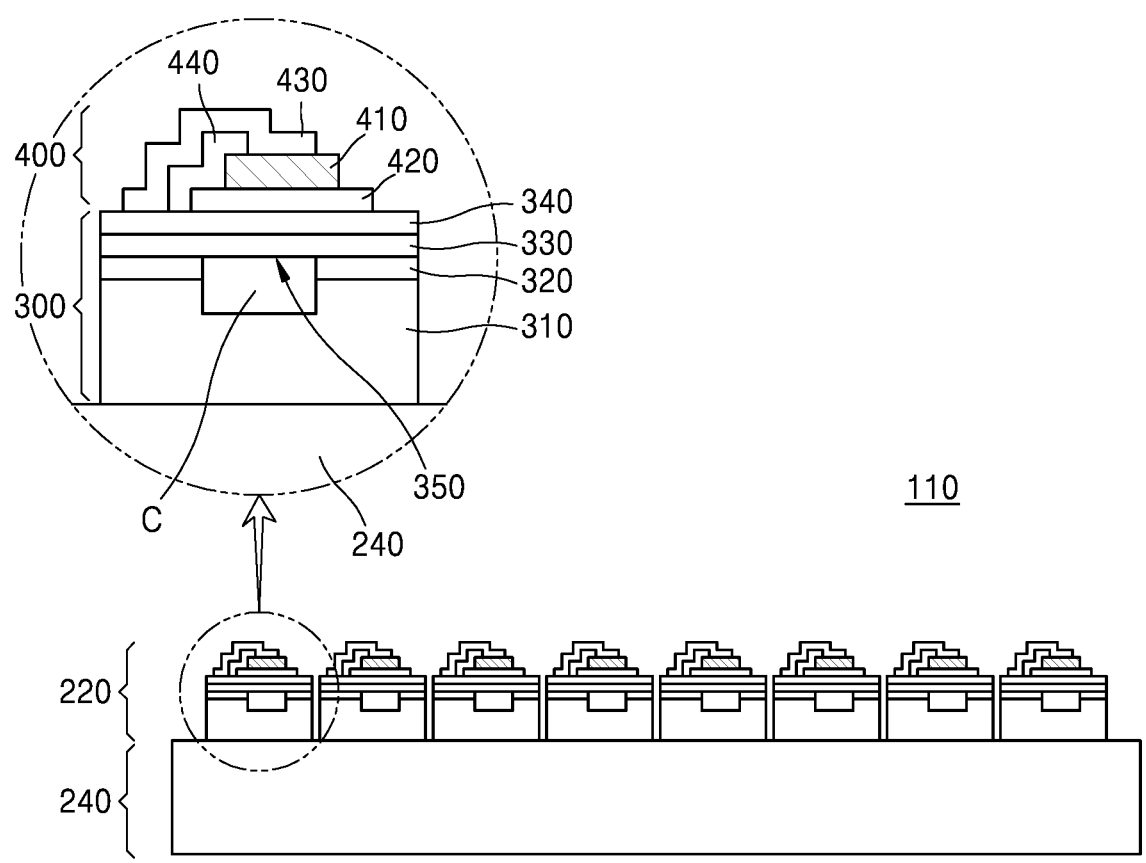
FIG. 3 is a schematic diagram of a physical configuration of the ultrasonic probe of FIG. 1.

FIG. 3 is a schematic diagram of a physical configuration of the ultrasonic probe 110 of FIG. 2. Referring to FIG. 3, the ultrasonic probe 110 may include the transducer 220 for converting electrical signals into ultrasound waves or ultrasound echoes back into electrical signals and a circuit substrate 240 for providing or receiving electrical signals to or from the transducer 220. In this case, ultrasound echoes are ultrasound waves reflected from the object, and are also referred to as ultrasound waves. The transducer 220 shown in FIG. 3 may be a piezoelectric micromachined ultrasonic transducer (pMUT).

The transducer 220 may include a plurality of unit substrates 300, each having a cavity C formed therein, and a plurality of transducer cells 400 respectively arranged on the unit substrates 300 and each including a piezoelectric layer 410. A plurality of cavities C respectively included in the plurality of unit substrates 300 may correspond one-to-one to the transducer cells 400. Although FIG. 3 shows that each of the plurality of unit substrates 300 may include one cavity C which corresponds to each transducer cell 400, embodiments are not limited thereto. For example, each of the plurality of unit substrates 300 may include one cavity C corresponding to some of the plurality of transducer cells 400.

The plurality of unit substrates 300 may be spaced apart from one another, and be arranged in a 2D or 1D array. Alternatively, the plurality of unit substrates 300 may be arranged in various other shapes such as a circle or polygon.

Each of the plurality of unit substrates 300 may include a silicon on insulator (SOI) structure. In this case, the SOI structure may be a structure in which a first silicon wafer 310, a first insulating layer 320, and a silicon thin layer 330 are sequentially stacked. For example, the first insulating layer 320 may include oxide or nitride, and may be formed of silicon oxide. The first silicon wafer 310 may have a thickness of about 30 µm to about 150 µm. The silicon thin layer 330 may have a thickness less than or equal to 10 µm. Since the first silicon wafer 310 is thin, it is possible to realize a thin film transducer. Each of the plurality of unit substrates 300 may further include a second insulating layer 340 on the silicon thin layer 330. Like the first insulating layer 320, the second insulating layer 340 may include oxide or nitride and may be formed of silicon oxide.

Each of the plurality of unit substrates 300 may include the cavity C formed by a groove in the first silicon wafer 310 and an opening in the first insulating layer 320. In other words, the first silicon layer 310 having the groove, the first insulating layer 320 having the opening, and the silicon thin layer 330 are combined to form the cavity C. The cavity C may be in a vacuum state, but is not limited thereto.

The cavity C may serve to absorb shock during vibration of the transducer cell 400. In other words, since the silicon thin layer 330 and the second insulating layer 340 overlying the cavity C are thin, they may vibrate in a direction perpendicular to the unit substrate 300 as the transducer cell 400 vibrates. Thus, a region of the silicon thin layer 330 overlying the cavity C may be referred to as a vibrating member 350. The vibrating member 350 may have a cross-sectional shape corresponding to that of the cavity C. For example, the vibrating member 350 may have a circular or polygonal shape, but is not limited thereto.

The transducer 220 may include the plurality of transducer cells 400 that convert electrical signals into ultrasound waves and vice versa. The plurality of transducer cells 400 may be spaced apart from one another. Each of the plurality of transducer cells 400 may include the piezoelectric layer 410 and first and second electrodes 420 and 430 separated from each other so that the piezoelectric layer 410 is disposed therebetween. The piezoelectric layer 410 may be formed of a material that may induce a piezoelectric effect. The material may include at least one of zinc oxide (ZnO), aluminum nitrate (AlN), lead zirconate titanate (Pb(Zr, Ti)$O_3$ or PZT), lead lanthanum zirconate titanate ((Pb,La)(Zr,—Ti)$O_3$ or PLZT), barium titanate (BaTi$O_3$ or BT), lead titanate (PbTi$O_3$ or PT), lead magnesium niobate (Pb(Mg$_{1/3}$Nb$_{2/3}$)$O_3$ or PMN)-PT, lead niobium zirconate titanate (Pb(Nb, Zr, Ti)$O_3$ or PNZT), etc. The piezoelectric layer 410 may have a thickness of less than or equal to about 10 μm. The first and second electrodes 420 and 430 may be formed of an electrically conductive material. The first and second electrodes 420 and 430 may be each formed of a metal such as gold (Au), copper (Cu), tin (Sn), silver (Ag), aluminum (Al), platinum (Pt), titanium (Ti), nickel (Ni), chromium (Cr), molybdenum (Mo), iridium (Ir), or combinations thereof.

Each of the plurality of transducer cells 400 may further include a third insulating layer 440 that is interposed between the first and second electrodes 420 and 430 and prevents conduction of an electric current between the first and second electrodes 420 and 430. For example, the third insulating layer 440 may cover at least some regions of the piezoelectric layer 410 and the first electrode 420. Furthermore, the second electrode 430 may extend over the third insulating layer 440 while being connected to the piezoelectric layer 410.

The ultrasonic probe 110 may further include a circuit substrate 240 for transmitting or receiving an electrical signal to or from the transducer 220. As described above, the circuit substrate 240 means a substrate including at least one chip for processing an electrical signal. For example, at least one chip for performing operations of the receiver 230 and the transmitter 210 may be formed on the circuit substrate 240. The circuit substrate 240 may be a flexible printed circuit board (FPCB). The ultrasonic probe 110 may further include a backing layer (not shown) underlying the circuit substrate 240. The backing layer may be provided on a rear surface of the circuit substrate 240 to support the circuit substrate 240. The backing layer and the circuit substrate 240 are separate components, but embodiments are not limited thereto. A substrate of the circuit substrate 240 may be formed of a backing material, and thus, the circuit substrate 240 may serve as a backing layer. According to the present embodiment, since the transducer 220 is a pMUT, the transducer 220 may not include a backing layer. The transducer 220 and the circuit substrate 240 may be electrically connected to each other via an electrically conductive material such as an electrically conductive bump and an electrically conductive pad.

Figure 4A:
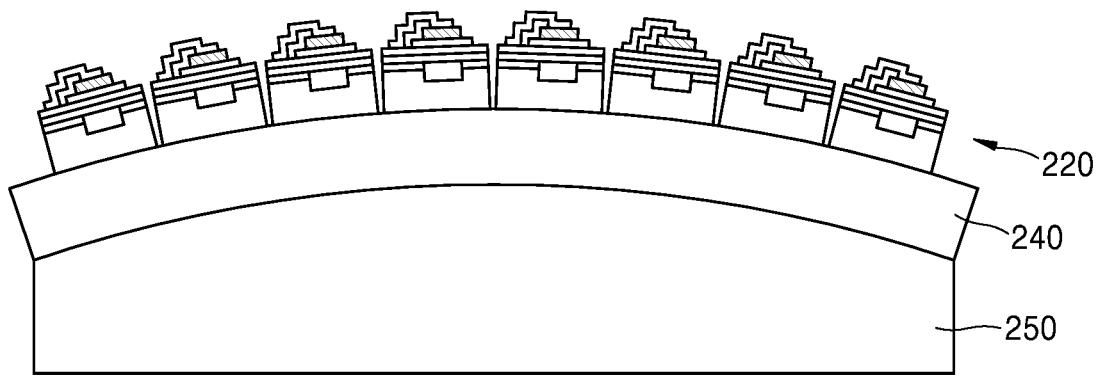
FIGS. 4A and 4B illustrate curved ultrasonic probes according to embodiments.
Figure 4B:
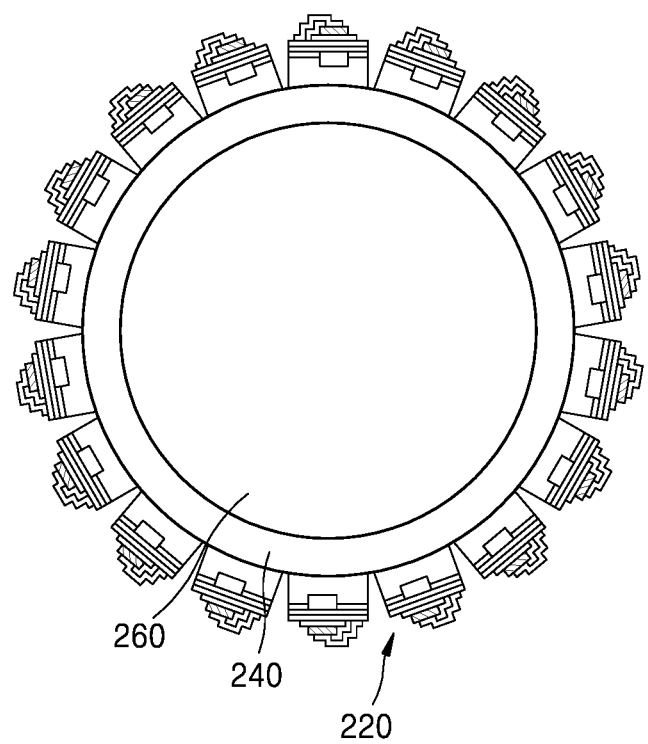

According to an embodiment, since the ultrasonic probe 110 includes the transducer cells 400 having a small size and the circuit substrate 240 that is the FPCB, the transducer 220 and the circuit substrate 240 may be provided on a support member of various shapes FIGS. 4A and 4B illustrate curved ultrasonic probes according to embodiments. Referring to FIG. 4B, the ultrasonic probe 110a may further include a support member 250 having a curved surface. For example, the circuit substrate 240 onto which the transducer 220 is fixed may be bonded to the curved surface of the support member 250. Since the circuit substrate 240 is flexible, and each of the transducer cells 400 has a small size, an adhesive force between the circuit substrate 240/the transducer 220 and the curved surface may be high. Alternatively, referring to FIG. 4B, the circuit substrate 240 and the transducer 220 may be fixed onto a spherical support member 260, and thus, a compact ultrasonic probe 110b may be achieved. Furthermore, utilization of the ultrasonic probe 110b in a spherical form may be increased due to a large radiation angle of ultrasound waves.

FIGS. 5 through 15 are reference diagrams for explaining a method of manufacturing the ultrasonic probe 110 of FIG. 3, according to an embodiment.

Figure 5:
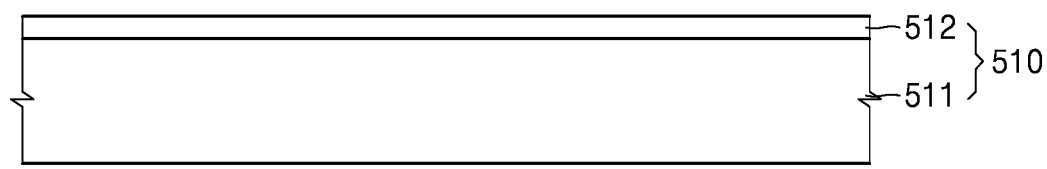
FIGS. 5 through 15 are reference diagrams for explaining a method of manufacturing an ultrasonic probe, according to an embodiment.

As shown in FIG. 5, a first substrate 510 may be prepared by forming a first insulating layer 512 over a first silicon wafer 511. The first insulating layer 512 may be formed of silicon oxide.

Figure 6:
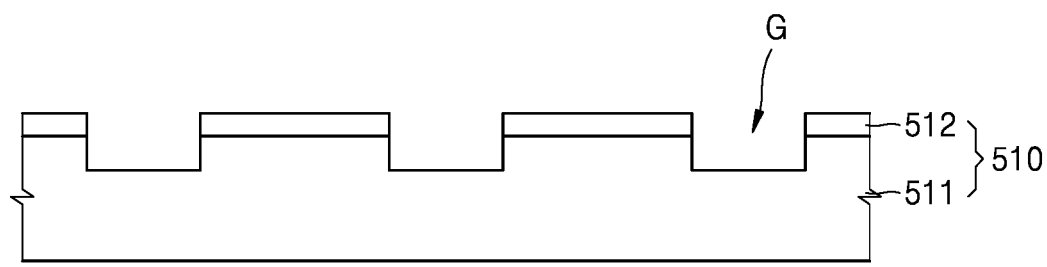

As shown in FIG. 6, a plurality of grooves G may be formed in the first substrate 510 by etching some regions of the first insulating layer 512 and the first silicon wafer 511. For example, the first insulating layer 512 and the first silicon wafer 511 may be patterned using a photolithographic technique. Alternatively, etching techniques may be used during patterning. For example, etching may be performed on the first insulating layer 512 to form openings that pass through the first insulating layer 512, and deep reactive ion etching (DRIE) may be performed on the first silicon wafer 511 to form grooves extending down from the openings.

Figure 7:
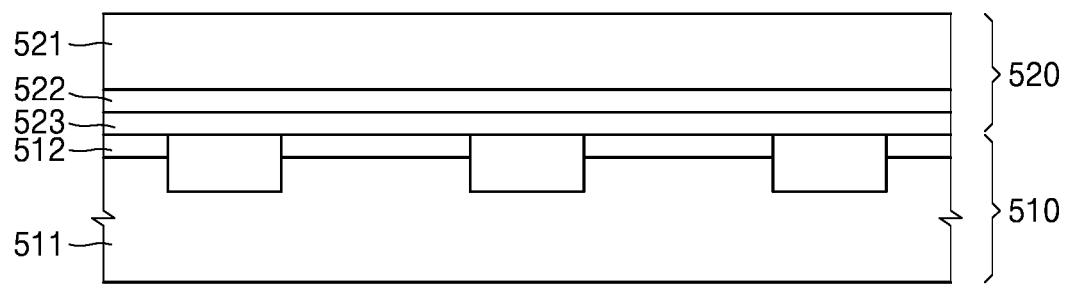

As shown in FIG. 7, the first substrate 510 may be bonded to a second substrate 520 having an SOI structure. The second substrate 520 may include a second silicon wafer 521, a third insulating layer 522, and a silicon thin layer 523. The first substrate 510 may be bonded to the second substrate 520 by using a silicon direct bonding (SDB) technique. The grooves G in the first substrate 510 may be respectively turned into a plurality of cavities C by bonding the second substrate 520 to the first substrate 510.

Figure 8:
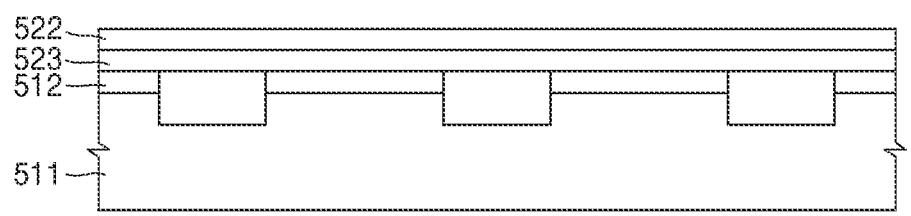

As shown in FIG. 8, the second silicon wafer 521 may be removed from the second substrate 520 so that the second insulating layer 522 and the silicon thin layer 523 may remain on the second substrate 520. For example, the second silicon wafer 521 may be removed using lapping, polishing, and wet etching techniques.

After removing the second silicon wafer 521 from the second substrate 520, a plurality of transducer cells may be formed on the second insulating layer 522. The plurality of transducer cells may respectively correspond to the plurality of cavities C. However, embodiments are not limited thereto, and the plurality of transducer cells may correspond to one of the plurality of cavities C.

Figure 9:
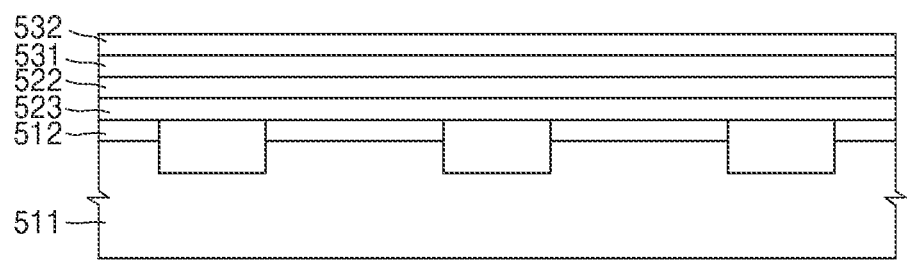

In detail, referring to FIG. 9, an electrically conductive material 531 and a piezoelectric material 532 may be sequentially formed over the second insulating layer 522.

The electrically conductive material 531 may be formed using a deposition technique. The piezoelectric material 532 may be formed using at least one of coating and growth techniques. The electrically conductive material 531 may be a metal such as Au, Cu, Sn, Ag, Al, Pt, Ti, Ni, Cr, Mo, Ir, or combinations thereof. The piezoelectric material 532 may include at least one of ZnO, AlN, PZT, PLZT, BT, PT, PMN-PT, PNZT, etc., and may have a thickness of less than or equal to about 10 μm.

Figure 10:
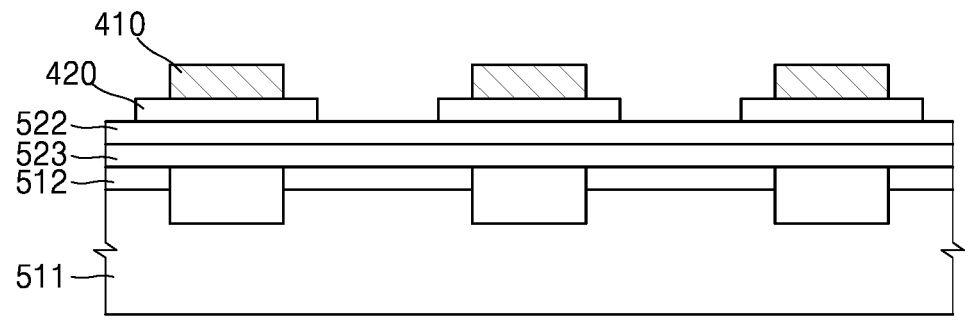

Subsequently, as shown in FIG. 10, the electrically conductive material 531 and the piezoelectric material 532 may be patterned to form a first electrode 420 and a piezoelectric layer 410, respectively. For example, the first electrode 420 and the piezoelectric layer 410 may be formed using a photolithographic technique.

Figure 11:
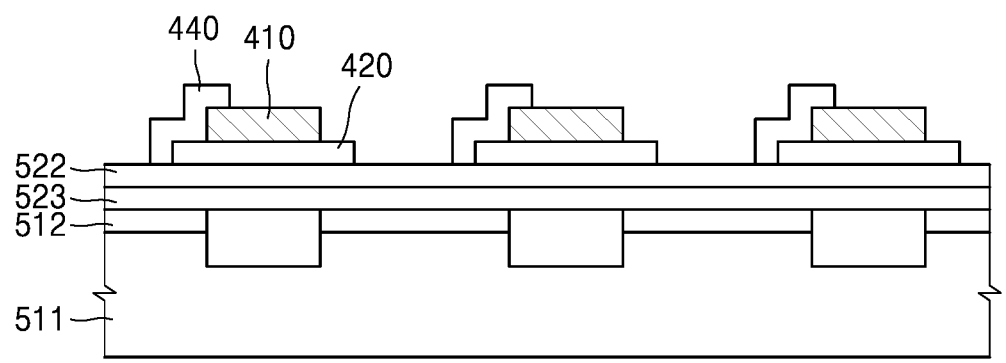
Figure 12:
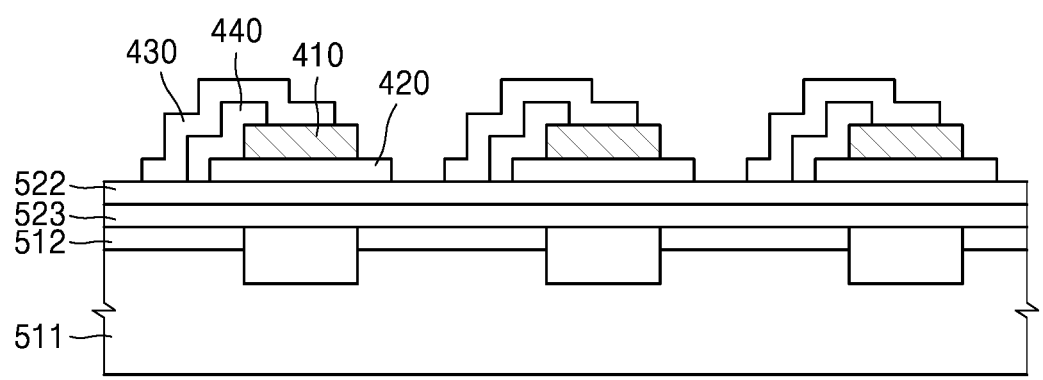

Then, as shown in FIG. 11, a third insulating layer 440 may be formed to cover regions of the first electrode 420 and the piezoelectric layer 410, and as shown in FIG. 12, a second electrode 430 may be formed to extend over the third insulating layer 440 while contacting a region of the piezoelectric layer 410. An insulating material may be formed on the first electrode 420 and the piezoelectric layer 410 and then patterned to form the third insulating layer 440. Furthermore, an electrically conductive material may be formed on the piezoelectric layer 410 and the third insulating layer 440 and then patterned to form the second electrode 430. The transducer 220 of FIG. 3 thus fabricated is a thin-film transducer that is highly flexible.

Figure 13:
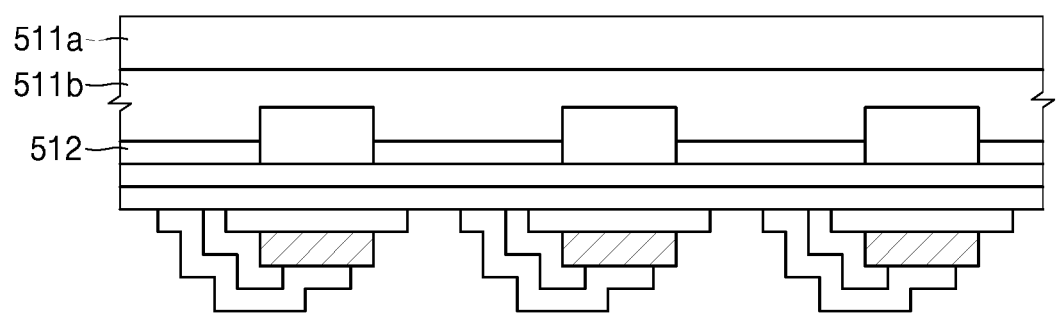

In addition, as shown in FIG. 13, a thickness of the first silicon wafer 511 in the first substrate 510 may be reduced. A structure shown in FIG. 13 is an inverted version of the structure shown in FIG. 12. In other words, a part 511a of the first silicon wafer 511 may be removed after turning the structure shown in FIG. 12 upside down. The thickness of the first silicon wafer 512 may be reduced by using grinding or chemical mechanical polishing (CMP). For example, a first silicon wafer having a thickness of 100 to 400 μm may be processed to form a first silicon wafer 511b having a thickness of 30 to 150 μm. Use of the first silicon wafer 511b having a reduced thickness may result in the transducer 220 being thinner. Due to the reduced thickness of the first silicon wafer 511, flexibility of the ultrasonic probe may be increased.

Figure 14:
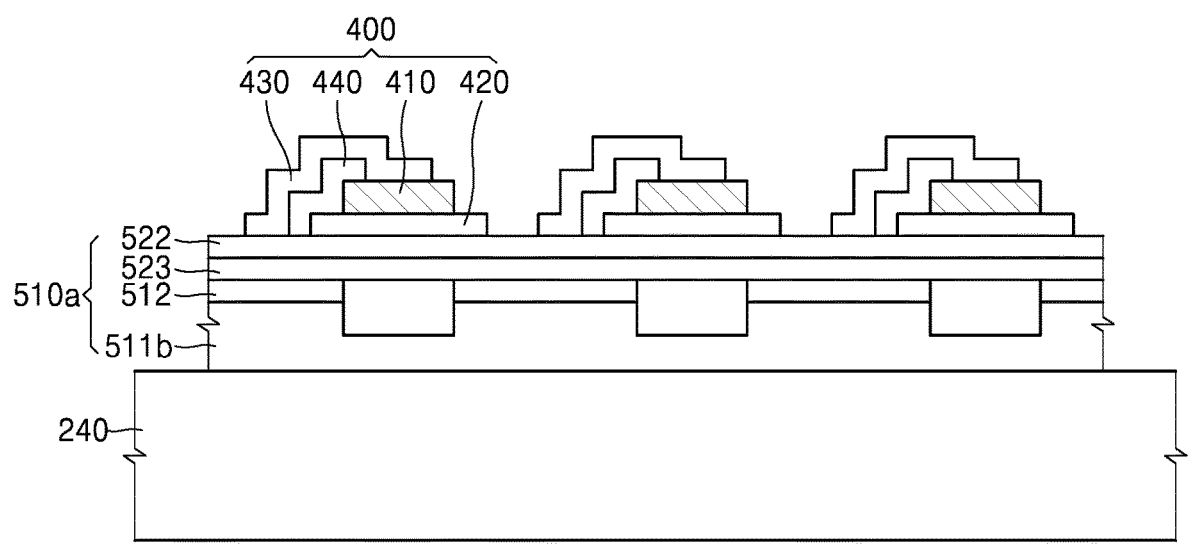

After flipping the structure of FIG. 13 back to its original position, as shown in FIG. 14, a first substrate 510a having transducer cells 400 formed thereon may be bonded to a circuit substrate 240. —For example, a bottom surface of the first substrate 510a may be bonded to a top surface of the circuit substrate 240 via an electrically conductive pad, an electrically conductive bump, etc. The circuit substrate 240 may be a FPCB.

Figure 15:
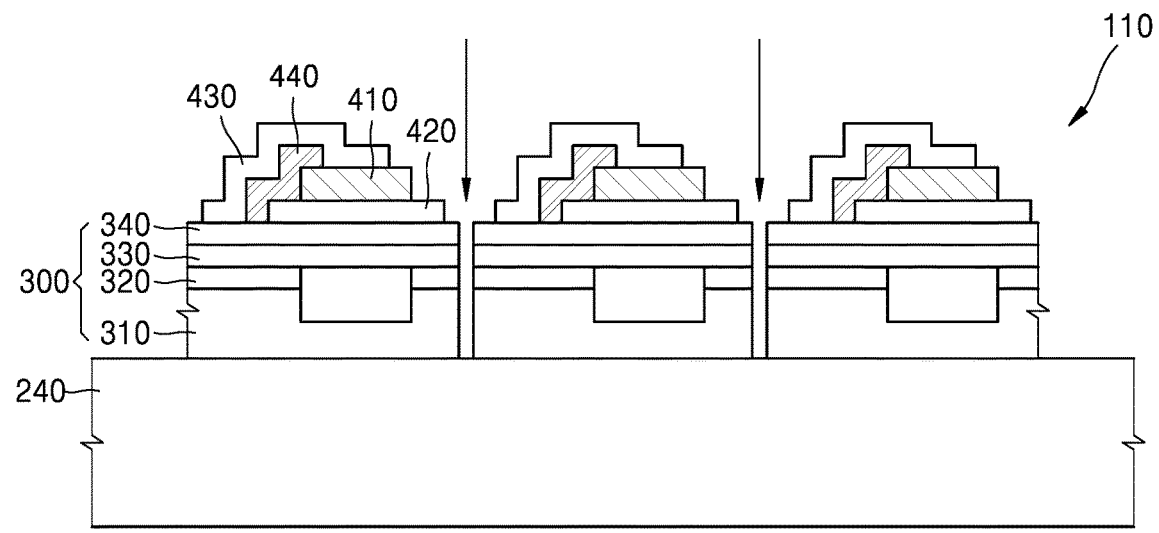

Thereafter, as shown in FIG. 15, a plurality of unit substrates 300 may be formed by respectively cutting the first substrate 510a, the silicon thin layer 523, and the second insulating layer 522. By removing regions of the first substrate 510a and the silicon thin layer 523 that do not overlap the transducer cells 400, the plurality of unit substrates 300 may be formed from the first substrate 510a, the silicon thin layer 523, and the second insulating layer 522. The plurality of unit substrates 300 may be formed by performing DRIE. Each of the plurality of unit substrates 300 may include an SOI structure composed of a first silicon wafer 310, a first insulating layer 320, and a silicon thin layer 330 and further include a second insulating layer 340. Since a kerf between the transducer cells 400 is formed using DRIE, the kerf may be less than gaps formed using other methods such as a cutting technique.

The ultrasonic probe 110 shown in FIG. 15 may be formed to have various shapes by attaching the ultrasonic probe 200 to a component such as a support member. The support member may have a flat or curved surface. Alternatively, by bonding the ultrasonic probe 110 to a spherical support member, the ultrasonic probe 110 may be formed as a spherical ultrasonic probe.

Since a transducer is formed on a silicon wafer as described above, it is possible to configure an ultrasonic probe into various shapes. Furthermore, an ultrasonic probe employing a pMUT according to an embodiment may be inserted into an object for diagnosis since the ultrasonic probe may operate at a low electrical power.

While ultrasonic probes and methods of manufacturing the ultrasonic probes according to one or more embodiments of the present disclosure have been described with reference to the appended figures, it will be understood by those of ordinary skill in the art that the present disclosure is not limited to the above-described embodiments but is intended to cover various changes in form and details and other embodiments such as equivalent arrangements within the scope of the appended claims. Accordingly, the true scope of the present disclosure should be determined based on the appended claims.

What is claimed is:

1. A method of manufacturing an ultrasonic probe, the method comprising:
    forming a plurality of grooves by removing regions of a first insulating layer and a first silicon wafer from a first substrate including the first silicon wafer and the first insulating layer;
    bonding a second substrate including a second silicon wafer, a second insulating layer, and a silicon thin layer to the first substrate, such that the plurality of grooves turn into a plurality of cavities;
    removing the second silicon wafer from the second substrate;
    forming transducer cells on regions of the second insulating layer corresponding to the plurality of cavities;
    removing a part of the first silicon wafer not comprising the plurality of cavities for the first silicon wafer to have a thickness of 30 μm to 150 μm after removing the part of the first silicon wafer; and
    forming a plurality of unit substrates by cutting the first substrate, the silicon thin layer, and the second insulating layer.

2. The method of claim 1, wherein the forming of the transducer cells comprises:
    sequentially forming an electrically conductive material and a piezoelectric material on the second insulating layer;
    forming a first electrode and a piezoelectric layer by respectively patterning the electrically conductive material and the piezoelectric material; and
    forming a second electrode on the piezoelectric layer.

3. The method of claim 2, wherein the piezoelectric layer has a thickness of less than or equal to 10 μm.

4. The method of claim 2, further comprising, before forming the second electrode, forming a third insulating layer covering the piezoelectric layer and the first electrode.

5. The method of claim 1, wherein the plurality of unit substrates are formed by deep reactive ion etching.

6. The method of claim 1, wherein the forming of the plurality of unit substrates comprises forming the plurality of unit substrates so that one or more transducer cells are provided for each of the plurality of unit substrates.

7. The method of claim 1, wherein the forming of the plurality of unit substrates comprises forming the plurality of unit substrates by removing regions of the first substrate, the silicon thin layer, and the second insulating layer that do not overlap the transducer cells.

8. The method of claim 1, further comprising bonding the first substrate to a circuit substrate before forming the plurality of unit substrates.

9. The method of claim 8, wherein the circuit substrate is flexible.

10. The method of claim 9, further comprising bonding the circuit substrate to a curved frame.

11. The method of claim 10, wherein the frame has a spherical shape.

* * * * *